United States Patent
Leonhardt et al.

(10) Patent No.: US 10,695,563 B2
(45) Date of Patent: Jun. 30, 2020

(54) ORTHODONTIC TREATMENT

(71) Applicant: CalXStars Business Accelerator, Inc., Santa Monica, CA (US)

(72) Inventors: Howard J. Leonhardt, Salt Lake City, UT (US); Jorge Genovese, Buenos Aires (AR); John Joseph Marchetto, Weston, FL (US)

(73) Assignee: CALXSTARS BUSINESS ACCELERATOR, INC., Santa Monica, CA (US)

( * ) Notice: Subject to any disclaimer, the term of this patent is extended or adjusted under 35 U.S.C. 154(b) by 0 days.

(21) Appl. No.: 15/471,954

(22) Filed: Mar. 28, 2017

(65) Prior Publication Data

US 2017/0274206 A1     Sep. 28, 2017

Related U.S. Application Data (60) Provisional application No. 62/314,240, filed on Mar. 28, 2016.

(51) Int. Cl.
*A61N 1/32* (2006.01)
*A61C 7/08* (2006.01)
(Continued)

(52) U.S. Cl.
CPC ............... *A61N 1/326* (2013.01); *A61C 7/00* (2013.01); *A61C 7/08* (2013.01); *A61N 1/0548* (2013.01)

(58) Field of Classification Search
CPC .......... A61C 5/70; A61C 7/08; A61M 31/002; A61N 1/326; A61N 1/0548
See application file for complete search history.

(56) References Cited

U.S. PATENT DOCUMENTS 4,976,733 A  12/1990  Girardot
5,543,318 A   8/1996  Smith et al.
(Continued)

FOREIGN PATENT DOCUMENTS

CA   2685161 A1  10/2007
EP   0603451 A1   6/1994
(Continued)

OTHER PUBLICATIONS

Chang et al. Effect of Pulse-Burst Electromagnetic Field Stimulation on Osteoblast Cell Activities; Bioelectromagnetics 25:457-465 (2004).*

(Continued)

*Primary Examiner* — Yogesh P Patel
*Assistant Examiner* — Stephen R Sparks
(74) *Attorney, Agent, or Firm* — TraskBritt (57) ABSTRACT

Described is a bioelectric stimulating device for reducing orthodontic treatment time (braces) with post-treatment stability enhancement. The device and associated methods provide a native sustainable optimal release of an increase in the quantity of the right cells and proteins over time and in the right sequence to optimize tooth movement with the braces by accelerating bone resorption at the leading edge of the tooth during movement. This acceleration phenomenon is responsible for being able to shorten orthodontic treatment time. Following the final alignment of the teeth, the same device can utilize the native response and accelerate the tooth/bone interface stability by targeting specific cells and proteins that are responsible for bone deposition (hardening) in order to shorten the retention phase, while greatly decreasing the chance of relapse (instability).

16 Claims, 1 Drawing Sheet

(51) Int. Cl.
*A61N 1/05* (2006.01)
*A61C 7/00* (2006.01)

(56) References Cited

U.S. PATENT DOCUMENTS

| | | | |
|---|---|---|---|
| 5,693,029 | A | 12/1997 | Leonhardt |
| 5,713,917 | A | 2/1998 | Leonhardt |
| 5,725,377 | A | 3/1998 | Lemler et al. |
| 6,344,052 | B1 | 2/2002 | Greenan et al. |
| 6,957,106 | B2 | 10/2005 | Schuler et al. |
| 6,988,004 | B2 | 1/2006 | Kanno et al. |
| 7,029,276 | B2 | 4/2006 | Mao |
| 7,341,062 | B2 | 3/2008 | Chachques et al. |
| 7,483,749 | B2 | 1/2009 | Leonhardt et al. |
| 7,686,799 | B2 | 3/2010 | Leonhardt et al. |
| 7,881,784 | B2 | 2/2011 | Pasricha et al. |
| 8,133,267 | B2 | 3/2012 | Leonhardt et al. |
| 8,639,361 | B2 | 1/2014 | Nathanson |
| 8,660,669 | B2 | 2/2014 | Nemeh et al. |
| 8,738,144 | B2 | 5/2014 | Schneider |
| 8,909,346 | B2 | 12/2014 | Chalmers |
| 8,945,104 | B2 | 2/2015 | Boone et al. |
| 9,032,964 | B2 | 5/2015 | Schuler et al. |
| 9,533,170 | B2 | 1/2017 | Dye et al. |
| 9,656,096 | B2 * | 5/2017 | Pilla ............ A61N 1/40 |
| 9,662,184 | B2 | 5/2017 | Lowe |
| 2003/0032998 | A1 | 2/2003 | Altman |
| 2003/0220556 | A1 | 11/2003 | Porat et al. |
| 2004/0010231 | A1 | 1/2004 | Leonhardt et al. |
| 2004/0115587 | A1 | 6/2004 | Breining et al. |
| 2004/0147906 | A1 * | 7/2004 | Voyiazis ............ A61B 5/0031 604/891.1 |
| 2005/0171578 | A1 | 8/2005 | Leonhardt |
| 2006/0030908 | A1 | 2/2006 | Powell et al. |
| 2007/0190028 | A1 * | 8/2007 | Qu ............ A61K 48/0058 424/93.2 |
| 2007/0265680 | A1 | 11/2007 | Liu et al. |
| 2008/0227046 | A1 | 9/2008 | Lowe et al. |
| 2010/0082027 | A1 | 4/2010 | Chalmers |
| 2010/0184183 | A1 * | 7/2010 | Schussler ............ A61L 27/24 435/177 |
| 2012/0156648 | A1 | 6/2012 | Kaufman et al. |
| 2013/0253413 | A1 * | 9/2013 | Levine ............ A61N 1/36053 604/20 |
| 2014/0023983 | A1 * | 1/2014 | Lowe ............ A61C 7/006 433/24 |
| 2014/0214115 | A1 | 7/2014 | Greiner et al. |
| 2014/0214116 | A1 | 7/2014 | Peterson et al. |
| 2014/0214124 | A1 | 7/2014 | Greiner et al. |
| 2014/0214144 | A1 | 7/2014 | Peterson et al. |
| 2017/0028184 | A1 | 2/2017 | Godden et al. |
| 2017/0266371 | A1 | 9/2017 | Leonhardt et al. |
| 2017/0274206 | A1 | 9/2017 | Leonhardt |
| 2018/0064935 | A1 | 3/2018 | Leonhardt et al. |
| 2019/0015661 | A1 | 1/2019 | Leonhardt et al. |
| 2019/0022389 | A1 | 1/2019 | Leonhardt |
| 2019/0022396 | A1 | 1/2019 | Leonhardt |

FOREIGN PATENT DOCUMENTS

| | | |
|---|---|---|
| WO | 2006/116728 A2 | 11/2006 |
| WO | 2007/146187 A2 | 12/2007 |
| WO | 2008/145724 A1 | 12/2008 |

OTHER PUBLICATIONS

Chang et al. Effect of Pulse-Burst Electromagnetic Field Stimulation on Osteoblast Cell Activities; Bioelectromagnetics 25:457-465 (2004) (Year: 2004).*
W. Hoffmann, "Regeneration of the gastric mucosa and its glands from stem cells", Curr Med Chem, 15(29):3133-44 (2008).
Yamaguchi, "RANK/RANKL/OPG during orthodontic tooth movement", Orthod Craniofac Res. May 2009; 12(2):113-9. doi: 10.1111/j.1601-6343.2009.01444.x.
Nimeri et al. "Acceleration of tooth movement during orthodontic treatment—a frontier in Orthodontics", Prog Orthod 2013; 14:42; DOI: 10.1186/2196-1042-14-42.
Dibart et al. "Tissue response during Piezocision-assisted tooth movement: a histological study in rats", Eur J Orthod (2014) 36 (4): 457-464; DOI: https://doi.org/10.1093/ejo/cjt079.
Khan et al. "Accelerating Tooth Movement: What Options We Have?" J Dent Health Oral Disord Ther 2016, 5(7): 00181.
Thattaliyath et al., "Modified Skeletal Myoblast Therapy for Cardiac Failure Using AAV SDF1", Proc. Intl. Soc. Mag. Reson. Med. 16, p. 579 (2008).
Prochazka et al., "Cocktail of Factors from Fat-derived Stem Cells Shows Promise for Critical Limb Ischemia" http://www.sciencenewsline.com/news/2016012204520017.html (Jan. 21, 2016).
Wei et al., "Epicardial FSTL1 reconstitution regenerates the adult mammalian heart," Nature 525: 479-485 (Sep. 24, 2015).
Hearts build new muscle with this simple protein patch, jacobsschool.ucsd.edu/news/news_releases/release.sfe?id=1813 (Sep. 16, 2015).
Stenn et al., "Bioengineering the Hair Follicle," Organogenesis, 3(1): 6-13 (Jan.-Mar. 2007).
Salcedo et al., "Low current electrical stimulation upregulates cytokine expression in the anal sphincter," Int. J. Colorectal Dis., Feb. 2012;27(2):221-5. doi: 10.1007/s00384-011-1324-3. Epub (Oct. 2011).
Marie Ellis, "Cure for baldness? Stem cells bring hope" http://www.medicalnewstoday.com/articles/271898.php.
Alice Park, "Shrinking Stem Cells Are the Real Reason for Hair Loss" Time, (Feb. 5, 2016).
Mass Device "Greatbatch wins FDA PMA for Algovita SCS" http://www.massdevice.com/greatbatch-wins-fda-pma-for-algovita-scs/ (Dec. 1, 2015).
P. Banerjee "Electrical muscle stimulation for chronic heart failure: an alternative tool for exercise training?" Curr Heart Fail Rep., 7(2):52-8. doi: 10.1007/s11897-010-0013-9 (Jun. 2010).
HN Sabbah "Electrical vagus nerve stimulation for the treatment of chronic heart failure", Cleve Clin J Med, 78 Suppl 1: S24-9. doi: 10.3949/ccjm.78.s1.04 (Aug. 2011).
Bio-Leonhardt "Micro Stimulator" http://www.bioleonhardt.com/micro-stimulator/.
Hu Klein, "Vagus Nerve Stimulation: A new approach to reduce heart failure" Cardiology Journal (2010).
Israeli innovation uses nerve stimulation to treat heart failure https://www.israel21c.org/israeli-innovation-uses-nerve-stimulation-to-treat-heart-failure/ (Feb. 11, 2007).
Sahoo and Losordo, "Exosomes and Cardiac Repair After Myocardial Infarction", Circulation Research, 114:333-344 (Jan. 16, 2014).
Tamaki et al., "Cardiomyocyte Formation by Skeletal Muscle-Derived Multi-Myogenic Stem Cells after Transplantation into Infarcted Myocardium", PLoS One 3(3): e1789. doi:10.1371/journal.pone.0001789 (Mar. 2008).
Electric Tumor Treatment Fields, No. 0827 Policy, http://www.aetna.com/cpb/medical/data/800_89910827.html (Nov. 18, 2016).
D. Grad, "Electrical Scalp Device Can Slow Progression of Deadly Brain Tumors", New York Times, https://www.nytimes.com/2014/11/16/health/electrical-scalp-device-can-slow-progression-of-deadly-brain-tumors.html?_r=0 (Nov. 15, 2014).
B. Borgobello, "FDA approves the treatment of brain tumors with electrical fields", New Atlas, http://newatlas.com/treatment-of-brain-tumors-with-electrical-fields/21433/ (Feb. 13, 2012).
Hopkins Medicine, "Overview of Pacemakers and Implantable Cardioverter Defibrillators (ICDs)", http://www.hopkinsmedicine.org/healthlibrary/conditions/cardiovascular_diseases/overview_of_pacemakers_and_implantable_cardioverter_defibrillators_icds_85,P00234/.
Medtronic "Cardiac Resynchronization Therapy (CRT) Devices for Heart Failure" http://www.medtronic.com/us-en/patients/treatments-therapies/crt-devices.html.
Columbia "Implant Procedure Concepts—Pacemaker, ICD and CRT Overview", http://www.columbia.edu/itc/hs/medical/hickey/docs/Pacemaker,%20ICD%20and%20CRT%20Overview%20022007.pdf.

(56) References Cited

OTHER PUBLICATIONS

FDA Approves Algovita Spinal Cord Stimulation System from Greatbatch, http://www.odtmag.com/contents/view_breaking-news/2015-12-02/fda-approves-algovita-spinal-cord-stimulation-system-from-greatbatch (Dec. 2, 2015).
Fukuoka et al., "The Latest Advance in Hair Regeneration Therapy Using Proteins Secreted by Adipose-Derived Stem Cells" The American Journal of Cosmetic Surgery, 29(4):273-282 (2012).
Reversing Age-Related Hair Loss and Restoring Healthy Hair Growth in Men and Women https://nutritionreview.org/2015/08/reversing-age-related-hair-loss-and-restoring-healthy-hair-growth-in-men-and-women/(Aug. 24, 2015).
Yamakazi et al., "Hair cycle-dependent expression of hepatocyte growth factor (HGF) activator, other proteinases, and proteinase inhibitors correlates with the expression of HGF in rat hair follicles", J Investig Dermatol Symp Proc., 4 (3):312-5 (Dec. 1999).
Involvement of hepatocyte growth factor/scatter factor and Met receptor signaling in hair follicle morphogenesis and cycling, FASEB J Feb. 2000 14:319-332.
Interesting study about prolactin, VEGF and angiogenic inhibition, http://www.regrowth.com/hair-loss-forums/topic/interesting-study-about-prolactin-vegf-and-angiogenic-inhibition/ (Nov. 2006).
Control of Hair Growth by a Growth Factor Protein, http://www.hairloss-reversible.com/control-of-hair-growth-by-a-growth-factor-protein/.
Hair Growth Factors, Nanogen, http://www.svijet-kose.com/dokumenti/Serum-vegf.pdf.
Blood Vessels Hold Key to Thicker Hair Growth, https://www.sciencedaily.com/releases/2001/02/010215074636.htm (Feb. 2001).
Jia et al., "Activin B Promotes Initiation and Development of Hair Follicles in Mice" Cells Tissues Organs, 198:318-326 (Feb. 2014).
Elastatropin® in Scalp & Hair Conditioning https://www.proteingenomics.com/haircare.html.
What Is Elastin? http://www.keracyte.com/index.php/site/page?view=whatIsElastin.
Park et al. "Effects of SM-215 on Hair Growth by Hair Follicle Stimulation", Indian Journal of Science and Technology, vol. 8(25), DOI: 10.17485/ijst/2015/v8i25/80263, (Oct. 2015).
Electrical brain stimulation could support stroke recovery https://www.sciencedaily.com/releases/2016/03/160316151108.htm (Mar. 16, 2016).
Robert Ferris, "Battle against baldness turns to stem cells" http://www.cnbc.com/2015/01/29/studies-indicate-its-possible-to-use-stem-cells-to-cure-baldness.html (Jan. 29, 2015).
Control of pelage hair follicle development and cycling by complex interactions between follistatin and activin, FASEB J (Jan. 2, 2003).
Chen et al., "Regenerative Hair Waves in Aging Mice and Extra-Follicular Modulators Follistatin, Dkk1, and Sfrp4," Journal of Investigative Dermatology, Aug. 2014, vol. 134, Issue 8, pp. 2086-2096.
Li et al., "Exogenous IGF-1 promotes hair growth by stimulating cell proliferation and down regulating TGF-β1 in C57BL/6 mice in vivo" Growth Hormone & IGF Research, vol. 24, Issues 2-3, pp. 89-94 (Apr.-Jun. 2014).
Our Approach to Improve Hair Loss by Increasing Hair Growth Factor IGF-1, http://www.jhgc.com.sg/theory/igf-1/index.html.
Hy et al., "Insulin-like growth factor 1 and hair growth," Dermatol Online J,; 5(2):1 (Nov. 1999).
Fukuoka and Suga, "Hair Regeneration Treatment Using Adipose-Derived Stem Cell Conditioned Medium: Follow-up With Trichograms" Eplasty, 15:e10 (Mar. 2015).
Signature Orthodontics "Accelerated Tooth Movement", http://www.sigortho.com/accelerated-tooth-movement.
Chang et al. "Pulsed electromagnetic fields stimulation affects osteoclast formation by modulation of osteoprotegerin, RANK ligand and macrophage colony-stimulating factor", Journal of Orthopaedic Research, 23 (2005) 1308-1314.
Apuzzo et al. "Biomarkers of Periodontal Tissue Remodeling during Orthodontic Tooth Movement in Mice and Men: Overview and Clinical Relevance", The Scientific World Journal, vol. 2013 (2013), Article ID 105873, 8 pages, http://dx.doi.org/10.1155/2013/105873.
Giganti et al. "Changes in serum levels of TNF-alpha, IL-6, OPG, RANKL and their correlation with radiographic and clinical assessment in fragility fractures and high energy fractures", J Biol Regul Homeost Agents, Oct.-Dec. 2012; 26 (4):671-80.
R. Hamman "Modulation of RANKL and Osteoprotegerin in Adolescents Using Orthodontic Forces", Masters Thesis, University of Tennessee (2010).
K. Hart, Katherine Ann D.D.S. , "RANKL and Osteoprotegerin Levels in Response to Orthodontic Forces" (2012). Theses and Dissertations (ETD). Paper 107. http://dx.doi.org/10.21007/etd.cghs.2012.0127.
Holding et al. "The correlation of RANK, RANKL and TNFa expression with bone loss volume and polyethylene wear debris around hip implants" Biomaterials 27(30):5212-9—Nov. 2006.
Jansen et al. "Stimulation of osteogenic differentiation in human osteoprogenitor cells by pulsed electromagnetic fields: an in vitro study" BMC Musculoskeletal Disorders (2010) 11:188 DOI: 10.1186/1471-2474-11-188.
Kanzaki et al. "Local RANKL gene transfer to the periodontal tissue accelerates orthodontic tooth movement", Gene Therapy, (2006) 13, 678-685.
Kanzaki et al. "Periodontal ligament cells under mechanical stress induce osteoclastogenesis by receptor activator of nuclear factor kappaB ligand up-regulation via prostaglandin E2 synthesis", J Bone Miner Res 2002;17:21✓ 220.
Kanzaki et al. "Local OPG gene transfer to periodontal tissue inhibits orthodontic tooth movement." J Dent Res 2004;83: 92✓ 925.
Kaur et al. "Electrically conductive polymers and composites for biomedical applications", RSC Adv., 2015,5, 37553-37567 DOI: 10.1039/C5RA01851J.
Keles et al. "Inhibition of tooth movement by osteoprotegerin vs. pamidronate under conditions of constant orthodontic force", Eur J Oral Sci. Apr. 2007;115(2):131-6.
Otero et al. "Expression and Presence of OPG and RANKL mRNA and Protein in Human Periodontal Ligament with Orthodontic Force", Gene-Regulation-and-Systems-Biology, 2016, 10, 15-20.
Seifi & Jeszri "Correlation of bone resorption induced by orthodontic tooth movement and expression of RANKL in rats", Dental Journal, vol. 26, No. 4 (2009).
Walsh & Choi "Biology of the RANK★ RAN☆ OPG System in Immunity, Bone, and Beyond", Front Immunol. 2014; 5: 511.
Zupan et al. "The relationship between osteoclastogenic and anti-osteoclastogenic pro-inflammatory cytokines differs in human osteoporotic and osteoarthritic bone tissues," Journal of Biomedical Science, 2012, 19:28 (DOI: 10.1186/1423-0127-19-28).
Spadari et al., Electrical stimulation enhances tissue reorganization during orthodontic tooth movement in rats; Clinical Oral Investigations, Jan. 2017, vol. 21, Issue 1, pp. 111-120.
Dong-Hwan Kim et al., The effects of electrical current from a micro-electrical device on tooth movement, Korean Orthod., Oct. 2008, 38(5):337-346, Abstract submitted in English.
Zhang et al. "Exosomes derived from human embryonic mesenchymal stem cells promote osteochondral regeneration", Osteoarthritis and Cartilage, vol. 24, Issue 12, Dec. 2016, pp. 2135-2140.
Prochazka et al. "Therapeutic Potential of Adipose-Derived Therapeutic Factor Concentrate for Treating Critical Limb Ischemia," Cell Transplantation, 25(9), pp. 1623-1633(11) (2016).
Mosteiro et al. "Tissue damage and senescence provide critical signals for cellular reprogramming in vivo." Science, 2016; 354 (6315): aaf4445 DOI: 10.1126/science.aaf4445.
Kim et al., The effects of electrical current from a micro-electrical device on tooth movement, http://e-kjo.org/search.php?where=aview &id=10.4041/kjod.2008.38.5.337& . . . visited Aug. 2, 2017.
Kanno et al., Establishment of a Simple and Practical Procedure Applicable to Therapeutic Angiogenesis, Circulation, 1999, pp. 2682-2687, vol. 99.
d'Apuzzo et al. "Biomarkers of Periodontal Tissue Remodeling during Orthodontic Tooth Movement in Mice and Men: Overview (56) References Cited

OTHER PUBLICATIONS and Clinical Relevance", The Scientific World Journal, vol. 2013 (2013), Article ID 105873, 8 pages, http://dx.doi.org/10.1155/2013/105873.
Chemet & Levin, "Transmembrane voltage potential is an essential cellular parameter for the detection and control of tumor development in a Xenopus model," Dis. Models & Mech. 6, pp. 595-607 (2013); doi:10.1242/dmm.010835.
Cerrada et al. "Hypoxia-Inducible Factor 1 Alpha Contributes to Cardiac Healing in Mesenchymal Stem Cells-Mediated Cardiac Repair," Stem Cells and Development, 22(3): 501-511 (2013).
Bradshaw et al. "Designer self-assembling hydrogel scaffolds can impact skin cell proliferation and migration" Nature Scientific Reports, vol. 4, Article No. 6903 (2014).
Barbault et al., Amplitude-modulated electromagnetic fields for the treatment of cancer: Discovery of tumor-specific frequencies and assessment of a novel therapeutic approach, Journal of Experimental & Clinical Cancer Research, Apr. 14, 2009, vol. 28, No. 51, doi:10.1186/1756-9966-28-51, 10 pages.
Vinod Krishnan, Ze'ev Davidovitch (eds.), Biological Mechanisms of Tooth Movement, (John Wiley & Sons 2015 (10 Pages).
Shoji-Matsunaga et al. "Osteocyte regulation of orthodontic force-mediated tooth movement via RANKL expression." Scientific Reports, 7: 8753, published online Aug. 18, 2017, DOI:10.1038/s41598-017-09326-7.
Miles et al. "Assessment of the changes in arch perimeter and irregularity in the mandibular arch during initial alignment with the AcceleDent Aura appliance vs no appliance in adolescents: A single-blind randomized clinical trial", Dec. 2016, vol. 150, Issue 6 American Journal of Orthodontics and Dentofacial Orthopedics (9 pages).
Li, et al. "Local injection of RANKL facilitates tooth movement and alveolar bone remodelling." Oral Diseases, 25(2), 550-560. https://doi.org/10.1111/odi.13013.
Wagenseil et al., "Elastin in large artery stiffness and hypertension," Journal of Cardiovascular Translational Research, vol. 5, No. 3, 2012, pp. 264-273, Available online at < https://www.ncbi.nlm.nih.gov/pmc/articles/PMC3383658/ >, 21, pages.
Stein et al., "The effect of transcutaneous electrical nerve stimulation on blood pressure," Blood Pressure, vol. 22, Issue 3, 2013, available online at < https://www.tandfonline.com/doi/full/10.3109/08037051.2012.722271 >, 5 pages.
Schardong et al., "Intradialytic neuromuscular electrical stimulation reduces DNA damage in chronic kidney failure patients: a randomized controlled trial," Biomarkers, vol. 23, Issue 5, 2018, pp. 1-11.
Niiranen et al., "Relative Contributions of Arterial Stiffness and Hypertension to Cardiovascular Disease: The Framingham Heart Study," Journal of the American Heart Association, vol. 5, No. 11, 2016, 8 pages.
Leonhardt's Launchpads Announces Filing of Patent for Bioelectric Stimulation Controlled Klotho Expression—Powerful Anti-aging and Regeneration Promoting Protein, by Api Podder, Published: Mar. 13, 2019.
Kanzaki et al. "Local OPG gene transfer to periodontal tissue inhibits orthodontic tooth movement." J Dent Res 2004; 83:92/925.
Almpani et al., "Nonsurgical Methods for the Acceleration of the Orthodontic Tooth Movement", Tooth Movement. Front Oral Biol., vol. 18, pp. 80-91 (Karger, Basel, CH 2016) (DOI:10.1159/000382048), Published online: Nov. 24, 2015.
Abstract of Zhang et al., "Comparison of arterial stiffness in non-hypertensive and hypertensive population of various age groups," Jan. 24, 2018, 2 pages.
Abstract of Sabino-Carvalho et al., "Non-invasive Vagus Nerve Stimulation Acutely Improves Blood Pressure Control in a Placebo Controlled Study," The FASEB Journal, vol. 31, 2017, available online at < https://www.fasebj.org/doi/abs/10.1096/fasebj.31.1_supplement.848.8 >, 2 pages.
Abstract of Collette et al., "Measurement of the local aortic stiffness by a non-invasive bioelectrical impedance technique," in Medical & Biological Engineering, vol. 49, No. 4, Feb. 2011, pp. 431-439, Available online at < https://www.ncbi.nlm.nih.gov/pubmed/21286830 >, 1 page.
Scott Jeffrey, "How to Decalcify Your Pineal Gland (and Why It's Really Important for Higher Mental Performance)," (available at https://scottjeffrey.com/decalcify-your-pineal-gland/), Retrieved on May 23, 2019, 23 pages.
Shahid et al., "Rhinosinusitis in Children," ISRN Otolaryngology, vol. 2012, Article ID 851831, (Dec. 2012), 11 pages.
Sharon M Moe, "Klotho: A Master Regulator of Cardiovascular Disease?," Circulation, vol. 125, (2012), pp. 2181-2183.
Shirtliff et al., "Assessment of the Ability of the Bioelectric Effect to Eliminate Mixed-Species Biofilms," Applied and Environmental Microbiology, vol. 71, (2005), pp. 6379-6382.
Somayaji et al., "In Vitro Scanning Electron Microscopic Study on the Effect of Doxycycline and Vancomycin on Enterococcal Induced Biofilm," Iranian Endodontic Journal, vol. 5, (2010), pp. 53-58.
Souli et al., "Effects of Slime Produced by Clinical Isolates of Coagulase-Negative *Staphylococci* on Activities of Various Antimicrobial Agents," Antimicrobial Agents and Chemotherapy, vol. 42, (Apr. 1998), pp. 939-941.
Stewart et al., "Electrolytic Generation of Oxygen Partially Explains Electrical Enhancement of Tobramycin Efficacy Against Pseudomonas aeruginosa Biofilm," Antimicrobial Agents and Chemotherapy, vol. 43, (1999), pp. 292-296.
Stoodley et al., "Influence of Electric Fields and pH on Biofilm Structure as Related to the Bioelectric Effect," Antimicrobial Agents and Chemotherapy, vol. 41, (1997), pp. 1876-1879.
Anne Trafton, "A Noninvasive Method for Deep Brain Stimulation," MIT News Office, (available at http://news.mit.edu/2017/noninvasive-method-deep-brain-stimulation-0601), (Jun. 1, 2017), 3 pages.
Aydin et al., "Focusing of Electromagnetic Waves by a Left-Handed Metamaterial Flat Lens," vol. 13, (2005), pp. 8753-8759.
Barker et al., "A Formidable Foe is Sabotaging Your Results: What You Should Know About Biofilms and Wound Healing," Plastic and Reconstructive Surgery, vol. 139, (2017), pp. 1184e-1194e.
Bioleohardnew, "Leonhardt Ventures Files Patent for Heart Valve Regeneration," (available at https://bioleonhardt.com/leonhardt-ventures-files-patent-for-heart-valve-regeneration/), (Mar. 20, 2018), 6 pages.
Chen et al., "The Role and Mechanism of (Alpha)-Klotho in the Calcification of Rat Aortic Vascular Smooth Muscle Cells," BioMed Research International, vol. 2015, (2015), 7 pages.
Chen et al., "The Strategy to Prevent and Regress the Vascular Calcification in Dialysis Patients," BioMed Research International, vol. 2017, (2017), 11 pages.
Chiang et al., "Silver-Palladium Surfaces Inhibit Biofilm Formation," Applied and Environmental Microbiology, vol. 75, (2009), pp. 1674-1678.
Costerton et al., "Mechanism of Electrical Enhancement of Efficacy of Antibiotics in Killing Biofilm Bacteria," Antimicrobial Agents and Chemotherapy, vol. 38, (1994), pp. 2803-2809.
Costerton et al., "The Application of Biofilm Science to the Study and Control of Chronic Bacterial Infections," The Journal of Clinical Investigation, vol. 112, (2003), pp. 1466-1477.
Delcaru et al., "Microbial Biofilms in Urinary Tract Infections and Prostatitis: Etiology, Pathogenicity, and Combating strategies," Pathogens, vol. 5, (2016), 12 pages.
Ehrlich et al., "Engineering Approaches for the Detection and Control of Orthopaedic Biofilm Infections," Clinical Orthopaedics and Related Research, vol. 437, (2005), pp. 59-66.
Froughreyhani et al., "Effect of Electric Currents on Antibacterial Effect of Chlorhexidine Against Entrococcus faecalis Biofilm: An in Vitro Study," Journal of Clinical and Experimental Dentistry, vol. 10, (Dec. 2018), pp. e1223-e1229.
Giladi et al., "Microbial Growth Inhibition by Alternating Electric Fields," Antimicrobial Agents and Chemotherapy, vol. 52, (2008), pp. 3517-3522.
Golberg et al., "Pulsed Electric Fields for Burn Wound Disinfection in a Murine Model," Journal of Burn Care & Research, vol. 36, (2015), pp. 7-13.

(56) References Cited

OTHER PUBLICATIONS

Hari et al., "Application of Bioelectric Effect to Reduce the Antibiotic Resistance of Subgingival Plaque Biofilm: An in Vitro Study," Journal of Indian Society of Periodontology, vol. 22, (2018), pp. 133-139.

Harkins et al., "Chitosan-Cellulose Composite for Wound Dressing Material. Part 2. Antimicrobial Activity, Blood Absorption Ability, and Biocompatibility," Journal of Biomedical Materials Research Part B, Applied biomaterials, vol. 102, (2014), 1199-1206.

Hleonhardt, Leonhardt Announces Vibrational Energy Device for Preventing Blood Clots Provisional Patent Application and License Agreements, (available at https://leonhardtventures.com/leonhardt-announces-vibrational-energy-device-preventing-blood-clots-provisional-patent-application-license-agreements/), (Jul. 5, 2017), 5 pages.

https://www.dicardiology.com/content/bioleonhardt-unveils-stem-pump Jan. 28, 2014.

Istanbullu et al., "Electrochemical Biofilm Control: Mechanism of Action," Biofouling, vol. 28, (2012), pp. 769-778.

Kasimanickam et al., "Prevention and Treatment of Biofilms by Hybrid- and Nanotechnologies," International journal of Nanomedicine, vol. 8, (2013), pp. 2809-2819.

Kim et al., "Effect of Electrical Energy on the Efficacy of Biofilm Treatment Using the Bioelectric Effect," NPJ Biofilms and Microbiomes, vol. 1, (2015), Article 15016, 8 pages.

Kinney et al., "High Intensity Focused Electromagnetic Therapy Evaluated by Magnetic Resonance Imaging: Safety and Efficacy Study of a Dual Tissue Effect Based Non-Invasive Abdominal Body Shaping," Lasers in Surgery and Medicine, vol. 51, (2019), pp. 40-46.

Lasserre et al., "Influence of Low Direct Electric Currents and Chlorhexidine Upon Human Dental Biofilms," Clinical and Experimental Dental Research, vol. 2, (Jul. 2016), pp. 146-154.

Lasserre et al., "Oral Microbes, Biofilms and Their Role in Periodontal and Peri-Implant Diseases," Materials, vol. 11, (Sep. 2018), Article 1802, 17 pages.

Lee et al. "Hepatocyte growth factor (HGF) activator expressed in hair follicles is involved in in vitro HGF-dependent hair follicle elongation," J. Dermatol. Sci., 25(2):156-63 (Feb. 2001).

Lee et al., "Targeted Release of Tobramycin From a pH-Responsive Grafted Bilayer Challenged With *S. aureus*," Biomacromolecules, vol. 16, (2015), pp. 650-659.

Lei et al., "Efficacy of Reversal of Aortic Calcification by Chelating Agents," Calcified Tissue International, vol. 93, (Nov. 2013), 15 pages.

Leibrock et al., "NH4Cl Treatment Prevents Tissue Calcification in Klotho Deficiency," Journal of the American Society of Nephrology, vol. 26, (2015), pp. 2423-2433.

Lop et al., Cutting-Edge Regenerative Medicine Technologies for the Treatment of Heart Valve Calcification, Calcific Aortic Valve Disease, (2013), (available at http://dx.doi.org/10.5772/55327), 57 pages.

Mclean et al., "Training the Biofilm Generation—a Tribute to J. W. Costerton," Journal of Bacteriology, vol. 194, (Dec. 2012), pp. 6706-6711.

Nodzo et al., "Cathodic Electrical Stimulation Combined With Vancomycin Enhances Treatment of Methicillin-Resistant *Staphylococcus aureus* Implant-Associated Infections," Clinical Orthopaedics and Related Research, vol. 473, (2015), pp. 2856-2864.

Nodzo et al., "Cathodic Voltage-Controlled Electrical Stimulation Plus Prolonged Vancomycin Reduce Bacterial Burden of a Titanium Implant-associated Infection in a Rodent Model," Clinical Orthopaedics and Related Research, vol. 474, (2016), 1668-1675.

Novickij et al., "Induction of Different Sensitization Patterns of MRSA to Antibiotics Using Electroporation," Molecules, vol. 23,(2018), Article 1799, 10 pages.

O'Neill et al., "Recent Progress in the Treatment of Vascular Calcification," Kidney International, vol. 78, (Dec. 2010), pp. 1232-1239.

Palza et al., "Electroactive Smart Polymers for Biomedical Applications," Materials, vol. 12, (2019), 24 pages.

Plumbingtoday, "How to Remove Hard, White Mineral Deposits from Faucets/Showerheads," (available at https://plumbingtoday.biz/blog/how-to-remove-hard-white-mineral-deposits-from-faucets-showerheads), (Jul. 11, 2016), 4 pages.

Pozo et al., "Bioelectric Effect and Bacterial Biofilms. A Systematic Review," The International Journal of Artificial Organs, vol. 31, (2008), pp. 786-795.

Pozo et al., "Effect of Electrical Current on the Activities of Antimicrobial Agents Against Pseudomonas aeruginosa, *Staphylococcus aureus*, and *Staphylococcus epidermidis* Biofilms," Antimicrobial Agents and Chemotherapy, vol. 53, (2009), pp. 35-40.

Pozo et al., "Prevention of *Staphylococcus epidermidis* Biofilm Formation Using Electrical Current," Journal of Applied Biomaterials & Functional Materials, vol. 12, (2014), pp. 81-83.

Pozo et al., "The Electricidal Effect: Reduction of *Staphylococcus* and Pseudomonas Biofilms by Prolonged Exposure to Low-Intensity Electrical Current," Antimicrobial Agents and Chemotherapy, vol. 53, (2009), pp. 41-45.

Ren et al., "Efficient Eradication of Mature Pseudomonas aeruginosa Biofilm via Controlled Delivery of Nitric Oxide Combined with Antimicrobial Peptide and Antibiotics," Frontiers in Microbiology, vol. 7, Article 1260, (Aug. 2016), 8 pages.

Roy et al., "Disposable Patterned Electroceutical Dressing (PED-10) Is Safe for Treatment of Open Clinical Chronic Wounds," Advances in Wound Care, vol. 8, (1019), pp. 149-159.

Sandvik et al., "Direct Electric Current Treatment under Physiologic Saline Conditions Kills *Staphylococcus epidermidis* Biofilms via Electrolytic Generation of Hypochlorous Acid," PloS one, vol. 8, (Feb. 2013), e55118, 14 pages.

Schmidt-Malan et al., "Activity of Fixed Direct Electrical Current in Experimental *Staphylococcus aureus* Foreign-Body Osteomyelitis," Diagnostic Microbiology and Infectious Disease, vol. 93, (2019), pp. 92-95.

Alghatrif et al. "The Conundrum of Arterial Stiffness, Elevated blood pressure, and Aging" Curr Hypertens Rep. Feb. 2015; 17(2): 12. doi: 10.1007/s11906-014-0523-z.

Bang et al., "Attenuation of Hypertension by C-Fiber Stimulation of the Human Median Nerve and the Concept-Based Novel Device," Scientific Reports, vol. 8, (2018), 12 pages.

Beitelshees et al. "CXCL5 polymorphisms are associated with variable blood pressure in cardiovascular disease-free adults" Hum Genomics. 2012; 6(1): 9.

Borden et al., "Electric Current-Induced Detachment of *Staphylococcus epidermidis* Biofilms from Surgical Stainless Steel," Applied and Environmental Microbiology, vol. 70, (2004), pp. 6871-6874.

Cai et al., "Intermedin Inhibits Vascular Calcification by Increasing the Level of Matrix (Gamma)-Carboxyglutamic Acid Protein," Cardiovascular Research, vol. 85, (2010), pp. 864-873.

Canty et al., "Antibiotics Enhance Prevention and Eradication Efficacy of Cathodic-Voltage-Controlled Electrical Stimulation against Titanium-Associated Methicillin-Resistant *Staphylococcus aureus* and Pseudomonas aeruginosa Biofilms," mSphere, vol. 4, (May/Jun. 2019), e00178-19, 14 pages.

Caubet et al., "A Radio Frequency Electric Current Enhances Antibiotic Efficacy Against Bacterial Biofilms," Antimicrobial Agents and Chemotherapy, vol. 48, (2004), vol. 4662-4664.

Chen et al., "Deficiency in the Anti-Aging Gene Klotho Promotes Aortic Valve Fibrosis Through AMPK(Alpha)-Mediated Activation of RUNX2," Aging Cell, vol. 15, (Oct. 2016), pp. 853-860.

Chen et al., Efficacy and Safety of Acupuncture for Essential Hypertension: A Meta-Analysis, Medical Science Monitor, vol. 24, (2018), pp. 2946-2969.

Cowburn et al. "HIF isoforms in the skin differentially regulate systemic arterial pressure" Proc Natl Acad Sci U S A. Oct. 22, 2013; 110(43): 17570-17575.

Eurekalert, UCI Study Finds Acupuncture Lowers Hypertension by Activating Natural Opioids, Available Online at < https://www.eurekalert.org/pub_releases/2016-10/uoc—usf103116.php >, (2016), 2 pages.

(56) References Cited

OTHER PUBLICATIONS

Fan et al., "A Review on the Nonpharmacological Therapy of Traditional Chinese Medicine with Antihypertensive Effects," Evidence-Based Complementary and Alternative Medicine, vol. 2019, (2019), Article ID 1317842, 7 pages.
Flachskampf et al., "Randomized Trial of Acupuncture to Lower Blood Pressure," Circulation, vol. 115, (2007), pp. 3121-3129.
Golberg et al., "Eradication of Multidrug-Resistant A. Baumannii in Burn Wounds by Antiseptic Pulsed Electric Field," Technology, vol. 2, (2014), pp. 153-160.
Greenwald "Pulse pressure and arterial elasticity" QJM: An International Journal of Medicine, vol. 95, Issue 2, 2002, pp. 107-112.
HEALTHCMI, "Acupuncture Combats Hypertension in University of California Research," Available online at < https://www.healthcmi.com/Acupuncture-Continuing-Education-News/1688-acupuncture-c . . . >, (2016), 9 pages.
HEALTHCMI, "Acupuncture Controls Hypertension in Groundbreaking Trial," Available online at < https://www.healthcmi.com/Acupuncture-Continuing-Education-News/1804-acupuncture-c . . . >, (2017), 9 pages.
HEALTHCMI, "UC Irvine—Acupuncture Reduces Hypertension Confirmed," Available Online at < https://www.healthcmi.com/Acupuncture-Continuing-Education-News/1792-uc-irvine-acup . . . >, (2017), 6 pages.
Leonhardt "Leonhardt Adds HIF-1 Alpha to Estate of Bioelectric Controlled Release Regenerative Proteins" Press Release, Published Jun. 13, 2017.
Li "Regulation of Renal Oxygenation and Blood Pressure" Art. Virginia Commonwealth University, Richmond, VA, United States (Abstract).
Li et al., "Long-Lasting Reduction of Blood Pressure by Electroacupuncture in Patients with Hypertension: Randomized Controlled Trial," Medical Acupuncture, vol. 27, No. 4, (2015), pp. 253-266.
Li et al., "Repetitive Electroacupuncture Attenuates Cold-Induced Hypertension through Enkephalin in the Rostral Ventral Lateral Medulla," Scientific Reports, vol. 6, (2016), 10 pages.
Li et al., "The Mechanism of Acupuncture in Treating Essential Hypertension: A Narrative Review," International Journal of Hypertension, vol. 2019, (2019), Article ID 8676490, 10 pages.
Longhurst et al. "Evidence-based blood pressure reducing actions of electroacupuncture: mechanisms and clinical application" Sheng Li Xue Bao. Oct. 25, 2017; 69(5): 587-597.
Nordstorm "Electrical Stimulation Blood Pressure Treatment Devices Market to Set Astonishing Growth by 2026" Art. Apr. 4, 2019 Gator Ledger.
Sahmeddini et al., "Electro-Acupuncture Stimulation at Acupoints Reduced the Severity of Hypotension During Anesthesia in Patients Undergoing Liver Transplantation," Journal of Acupuncture and Meridian Studies, vol. 5, Issue 1, (2012), pp. 11-14.
Sethi et al. "Aortic stiffness: pathophysiology, clinical implications, and approach to treatment" Integr Blood Press Control. 2014; 7: 29-34.
Spiridonov et al. "Effect of Transcutaneous Electrical Stimulation of Nerves on Blood Pressure and Blood Content of Neuropeptide CGRP and Nitric Oxide in Hypertensive Rats with Metabolic Disturbances" Bull Exp Biol Med (Feb. 2019) 166: 436-437.
Sultana et al., "Electrochemical Biofilm Control: A Review," Biofouling, vol. 31, (2015), pp. 745-758.
Szkotak et al., "Differential Gene Expression to Investigate the Effects of Low-Level Electrochemical Currents on Bacillus subtilis," AMB Express, vol. 1, (Nov. 2011), 12 pages.
Tan et al., "Acupuncture Therapy for Essential Hypertension: a Network Meta-Analysis," Annals of Translational Medicine, vol. 7, (2019), pp. 1-12.
Ucirvine, "Electroacupuncture for Hypertension in Women: The Susan Samueli Center for Integrative Medicine at UC Irvine is Recruiting Patients for a Study", Principle Investigators: Dr. Stephanie Tjen-a-Looi and Dr. Shaista Malik, MOD# 20266, HS# 1999-2222, (2017), 1 page.
Vilela-Martin et al., "Effects of Transcutaneous Electrical Nerve Stimulation (TENS) on Arterial Stiffness and Blood Pressure in Resistant Hypertensive Individuals: Study Protocol for a Randomized Controlled Trial," Trials, vol. 17, (2016), pp. 1-13.
Wang et al., "Controlling *Streptococcus mutans* and *Staphylococcus aureus* Biofilms With Direct Current and Chlorhexidine," AMB Express, vol. 7, (Nov. 2017), 9 pages.
Warner "Inflammation Adds to Blood Pressure Risks, High Blood Pressure and C-Reactive Protein May Trigger Heart Attack, Stroke" Art WebMD Health News (2003) 2 pages.
Welch "RGS2 Proteins Regulate Blood Pressure" JASN Nov. 2010, 21 (11) 1809-1810.
Wellman et al., "Bacterial Biofilms and the Bioelectric Effect," Antimicrobial Agents and Chemotherapy, vol. 40, (1996), pp. 2012-2014.
Wong et al., "Dual Functional Polyelectrolyte Multilayer Coatings for Implants: Permanent Microbicidal Base With Controlled Release of Therapeutic Agents," Journal of the American Chemical Society, vol. 132, (2010), pp. 17840-17848.
Wu et al., "Vascular Calcification: an Update on Mechanisms and Challenges in Treatment," Calcified Tissue International, vol. 93, (Oct. 2013), pp. 365-373.
Yang et al., "Acupuncture for hypertension," Cochrane Database of Systematic Reviews, Available Online at < https://www.cochranelibrary.com/cdsr/doi/10.1002/14651858.CD008821.pub2/full >, (2018), 4 pages.
Yang Lei, "Mechanisms and Reversal of Elastin Specific Medial Arterial Calcification" (2014). All Dissertations, Paper 1307, (available at https://tigerprints.clemson.edu/all_dissertations/1307), 214 pages.
Yarbrough et al., "Specific Binding and Mineralization of Calcified Surfaces by Small Peptides," Calcified Tissue International, vol. 86, (2010), pp. 58-66.
Yu et al. "Association between inflammation and systolic blood pressure in RA compared to patients without RA" Arthritis Research & Therapy vol. 20, Article No. 107 (2018).
Zalavras, Charalampos G. "CORR Insights(Registered): Cathodic Voltage-Controlled Electrical Stimulation Plus Prolonged Vancomycin Reduce Bacterial Burden of a Titanium Implant-associated Infection in a Rodent Model," Clinical Orthopaedics and Related Research, vol. 474, (2016), pp. 1676-1678.
Zhang et al., "Highly Stable and Reusable Imprinted Artificial Antibody Used for in Situ Detection and Disinfection of Pathogens," Chemical Science, vol. 6, (2015), pp. 2822-2826.

\* cited by examiner

ORTHODONTIC TREATMENT

CROSS-REFERENCE TO RELATED APPLICATIONS

This application claims the benefit under 35 USC § 119 of U.S. Provisional Patent Application Ser. No. 62/314,240, filed Mar. 28, 2016; the disclosure of which is incorporated herein in its entirety by this reference.

FIELD

The application relates generally to the field of dental devices and associated treatments, and more specifically to precise bioelectrical stimulation of a subject's tissue to shorten orthodontic treatment time (e.g., with braces).

BACKGROUND

Conventional orthodontic treatment ("braces") lasts on average from 22 to 24 months due to the fact that the teeth are housed in bone that must go through the resorption/demineralization (softening) process to allow the teeth to move. The longer the treatment takes, the more side effects are possible including permanent root length loss and/or gum and bone disease due to improper patient care.

Corticotomy is a widely accepted method for accelerating tooth movement to shorten treatment time but requires costly bone and gum surgery that can be painful and has significant associated morbidity.

Following orthodontic treatment, there is a prolonged period of retention while the bone deposition (hardening) takes place over the period of up to two years (retention). Orthodontic literature places instability/relapse at 30% or greater. Currently, there is long-term retention using retainers, both fixed and removable, which requires diligence and continued cooperation.

Prior art attempts to shorten orthodontic treatment time have proven ineffective, generally due to their inability to significantly increase the rate of tooth movement. Specific protein injection systems to enhance bone resorption have experienced a lot of wash out of the therapeutic agent, so continual re-injections are needed and are thus more painful and are prone to cause infections. Laser therapy systems and vibrational energy systems have been generally ineffective as described in orthodontic literature

BRIEF SUMMARY

Described is a system (device and method) that provides sustainable optimal protein release by a subject with an increase in the quantity of the correct cells and proteins over time and in the right sequence to optimize orthodontic tooth movement by accelerating bone resorption/demineralization at the leading edge of the tooth during movement. This acceleration phenomenon result in shortened orthodontic treatment times (e.g., the amount of time braces need to be worn by the subject).

Described is a bioelectric stem cell and protein stimulation device that reduces orthodontic treatment time by, e.g., half (or even more). The device and method provide sustainable optimal release of the cells and protein with an increase in the quantity of the ideal cells and proteins over time and in the right sequence to optimize orthodontic tooth movement by accelerating bone resorption/demineralization at the leading edge of the tooth during orthodontic movement. The bone is then re-mineralized on the trailing edge, and then fully once the teeth are in their corrected orthodontic positions for added stability.

The described system reduces the time necessary to effect a desired tooth movement, which can reduce the pain associated with tooth movement. It also reduces the tendency of teeth to relapse to their original positions after stopping the orthodontic treatment, and ultimately reduces the time in which unsightly braces need to be worn. The bioelectric stimulator targets the exact native bone resorption pathways that are necessary for tooth movement when an orthodontic force is applied. Specific proteins activate specific cells to cause the cells to initiate bone resorption. This stimulation allows for a greater expression of the specific proteins available that can activate the increased native pluripotent cells. This in turn activates and increases the process of differentiation of pluripotent cells into osteoclasts (bone resorbing cells). With these increases in the targeted bone resorption (softening), the teeth are able to move more rapidly, resulting in an increased rate of tooth movement.

The bioelectric stimulator is also used to enhance bone stability following tooth movement utilizing the bone deposition pathway. In the same manner as described for bone resorption, specific proteins stimulate specific cells to differentiate into osteoblasts (bone deposition cells) and thereby increase the quantity and quality of bone surrounding the teeth after orthodontic tooth movement. This can be done rapidly by expressing for the right proteins and cells at the right time to cut the stability time by up to one half.

Also described is a bioelectric stimulator programmed to activate release (in a subject) of nuclear factor kappa-B ligand ("RANKL"), tumor necrosis factor-alpha ("TNF-$\alpha$"), osteoprotegerin ("OPG"), stem cell homing factor ("SDF-1"), hepatocyte growth factor ("HGF"), insulin-like growth factor ("IGF-1"), vascular endothelial growth factor ("VEGF"), endothelial nitric oxide synthase ("eNOS"), and macrophage colony-stimulating factor ("M-CSF").

Bone resorption/deposition is a balance between the amount of RANKL verses OPG present. When RANKL is signaled for, there is still OPG present, which counteracts some of the RANKL so it is preferred to have significant over expression of RANKL and then conversely for OPG.

Pulsed electromagnetic fields to stimulate OPG and RANKL values are generally too low to make any type of a significant difference. Kanzaki et al. (2004); Kanzaki et al. (2002).

A preferred such system includes:

A bioelectric stimulator that controls/stimulates release/production of RANKL, TNF-alpha, OPG, SDF-1, HGF, IGF-1, VEGF, eNOS and M-CSF.

The most important and most difficult to achieve bioelectric signals are the ones that control stem cell differentiation into useful tissue. The bioelectric signals are also the ones that require the most precise control by the bioelectric stimulator.

The prior art systems fail to produce the correct proteins to attract and produce the right cells in the proper sequence to facilitate consistently increased tooth movement. Existing devices fail to consistently increase the necessary cells and proteins in sequence in order to accelerate the resorption/demineralization (softening) process in bone. Therefore these devices have a limited effect on increasing the rate of tooth movement.

For instance, the prior art (e.g., Jansen et al.) did not identify the optimal signals for RANKL and OPG. Their change values were under 30%. There was no control of protein expression. They did not use direct electrical conduction contact with gums to ensure greater signal purity delivery and superior results. There was too much drift in their signal, which in turn can cause bone formation in gums.

In the system hereof, the OPG signal directly stimulates osteoprogenitors towards osteogenic differentiation. The RANKL signal in the system hereof also decreases MT1-MMP expression.

Relating to the bioelectric stimulation-controlled release of receptor activator of NFk-B ligand ("RANKL" or "TNFSF11") among other proteins, including stem cell homing factor SDF-1, designed to accelerate tooth movement and cut in half the time required for orthodontic treatment with braces and clear aligners.

A bioelectric signal produces RANKL (Receptor activator of nuclear factor kappa-B ligand): 3 MV at 2/100 Hz alternating frequency with current of 3 ma.

This bioelectric signal may optionally be followed by: 15 Hz, 1 Gauss EM field, (e.g., applied at the orthodontist's office) consisting of 5-millisecond bursts with 5-microsecond pulses followed by 200-Mµs pulse duration @ 30 Hz and with current amplitude of 140 mA for minimum 20 to 45 minutes. The office use supplemental extra booster electromagnetic filed (Gaus signal) may be delivered wirelessly with no conduction elements in the subject's mouth.

A bioelectric signal produces OPG osteoprotegerin (also known as osteoclastogenesis inhibitory factor (OCIF), or tumor necrosis factor receptor superfamily member 11B (TNFRSF11B), is a protein that in humans is encoded by the TNFRSF11B gene) by bioelectric signal range 3 my to 5 my @ frequency range 1 to 3 MHz duration range 30 to 40 mW/cm$^2$ for a minimum of 20 to 45 minutes.

The system addresses the desire to reduce the time it takes to treat orthodontic patients, which would be a boon to them. This approach speeds up the normal process of bone demineralization in order to accelerate tooth movement. Prior art laser light and vibration devices have generally fallen short in providing a reliable pathway to the underlying mechanism of action for tooth movement. Also, repeat RANKL needle injection methods are painful for patients and needed too frequently. The described system provides clear cut, direct control for the release of essential cells and proteins needed for accelerating tooth movement, and with less pain. Additionally, it can be used in the areas of oral surgery and periodontal surgery for bone grafts to enhance the healing phase of the procedure. Additionally, it can be utilized to enhance the speed for integration of dental implants in bone.

Also, the device is applicable for use in craniofacial surgery where bone grafts are used to repair facial anomalies. Oral surgery can be benefited by the use of this device for repairing bones in orthognathic surgery, jaw fracture, bone plate insertion, various grafts, and implants. All these areas can benefit from the use of the device because it reduces the amount of discomfort from any of the procedures as the stem cell recruitment lessens the subject's pain.

DETAILED DESCRIPTION

The bioelectrical stimulation causes the subject's tissues to release SDF-1, M-CSF, RANKL, OPG, VEGF, IGF-1, and TNF-alpha, eNOS in greater quantities.

RANKL binds to the RANK receptor on the mesenchymal precursor cells to differentiate into Osteoclasts which are responsible for bone resorption/demineralization. TNF-alpha is another pathway similar to RANKL and acts in much the same way to cause differentiation of osteoclastic precursors into Osteoclasts. VEGF will increase blood supply by forming additional blood vessels to initially carry away the minerals and mineral salts during the resorption process (demineralization), on the leading side of tooth movement, and then carry the minerals back to the areas for remineralization on the trailing side, during tooth movement. Bringing these sequences of cells and proteins together can reduce up to 300%, the amount of time needed to wear orthodontic braces to finish the teeth straightening procedure.

It has been shown that RANKL injections accelerated by 2/3rds tooth movement and OPG—Osteoprotegerin—injections served to freeze tooth positions after movement. Zupan et al. "The relationship between osteoclastogenic and anti-osteoclastogenic pro-inflammatory cytokines differs in human osteoporotic and osteoarthritic bone tissues," *Journal of Biomedical Science*, 2012, 19:28 (DOI: 10.1186/1423-0127-19-28), the contents of which are incorporated herein by this reference. However, two to three time weekly needle injections need to be done by a doctor in an orthodontist's office are not well tolerated by most patients, have risk of infection, cause pain and have a high cost.

The described device and method produces the same volume of RANKL protein and OPG as the needle injection studies with only two 20 minute bioelectric protein expression with 3-4 stimulation sessions a week. The stimulation is pain free in fact it reduces any pain that may be present. The stimulation can be done in the subject's home, e.g., while watching TV or reading conveniently at a relatively low cost. There is virtually no risk of infection.

The device described herein provides sustainable optimal release with an increase in the quantity of the right cells and proteins over time and in the right sequence to optimize tooth movement by accelerating bone resorption/demineralization at the leading edge of the tooth during movement. This acceleration phenomenon is responsible for being able to shorten orthodontic treatment time significantly. Also, it can produce orthodontic tooth movement acceleration, orthodontic treatment tooth stabilization, and craniofacial bone graft healing acceleration and it has been shown that the teeth are able to move more rapidly, with research indicating an increased rate of up to 300%.

The bioelectric stimulator is also used to enhance bone stability following orthodontic tooth movement utilizing the bone deposition pathway. In the same manner as for bone resorption, the specific proteins stimulate the specific cells to differentiate into osteoblasts (bone deposition cells) and thereby increase the quantity and quality of bone surrounding the teeth after tooth movement. This can be done rapidly by expressing the right proteins and cells at the right time to cut the stability time by up to one third.

In certain embodiments, the method includes: placing a bioelectric stimulator having electrically associated therewith a conductive mouthpiece constructed to fit covering the teeth and against the dental gums of a subject via the conductive mouthpiece. The bioelectric stimulator is attached to and/or in electrical association with a conductive mouthpiece that fits adjacent to the respective teeth and gums. The conductive mouthpiece is typically made of an organic polymer that conducts electricity and is sized and shaped to fit the subject's teeth (see, FIG. 1). The bioelectric stimulator sends preprogrammed signals to the gum and bone tissue, e.g., via the conductive mouthpiece, for specific cell and protein expression during active tooth movement.

The bioelectric stimulator and conductive mouthpiece cause SDF-1 release in the subject as a cell homing signal to recruit mesenchymal stem cells from bone marrow and dental gums to become osteoclastic precursor cells. The stimulator causes SDF-1 release as a cell homing signal to recruit mesenchymal stem cells from bone marrow and gingival tissue (gums) to become osteoclastic precursor cells.

The bioelectric stimulator and conductive mouthpiece cause M-CSF release in the subject as a cell homing signal to recruit osteoclastic precursor cells from bone marrow and dental gums to differentiate into osteoclasts. The M-CSF is a cell homing signal to recruit osteoclastic precursor cells from bone marrow and gingival tissue (gums) to differentiate into osteoclasts.

Typically, one set of signals from the bioelectric stimulator will attract the cells in SDF-1 and M-CSF to increase the numbers of osteoclastic progenitor cells to the area of tooth movement.

The bioelectric stimulator and conductive mouthpiece cause an increase in the level of RANKL in the subject to allow the osteoclastic precursor cells to become osteoclasts and increase the rate of bone resorption/demineralization. The increased expression level of RANKL allows the osteoclastic precursor cells to become osteoclasts and multinucleated osteoclasts and thereby increase the bone resorption process.

The bioelectric stimulator and conductive mouthpiece cause VEGF to increase blood vessels and blood supply in the subject to carry the necessary proteins and minerals and mineral salts needed for bone resorption/demineralization and osteosynthesis. VEGF increases blood vessel formation and blood supply to carry the necessary proteins and mineral salts needed for bone resorption (softening).

The bioelectric stimulator and conductive mouthpiece cause IGF-1 release in the subject, which increases the rate of bone metabolism for bone resorption/demineralization and then the re-mineralization process.

The bioelectric stimulator and conductive mouthpiece cause release of TNF-alpha in the subject to help osteoclast differentiation, function and survival for the process of resorption/demineralization of bone on the leading edge of tooth movement. The TNF-alpha helps to induce osteoclast differentiation, function, and survival for the process of bone resorption on the leading edge of the tooth during movement.

The bioelectric stimulator and conductive mouthpiece cause OPG release to enhance osteoblast formation and bone formation/re-mineralization for tooth stability following orthodontic tooth movement.

Relationship Between the Components:

The bioelectric stimulator sends specific signal(s) to the tissue for cell and protein expression typically via the conductive mouthpiece.

SDF-1 and M-CSF release recruits an increased number of osteoclastic progenitor cells to the area of tooth movement.

RANKL and TNF-alpha direct the increased number of pre-osteoclastic cells to differentiate into osteoclasts and thereby accelerates the resorption/demineralization (softening) of bone.

VEGF is responsible for carrying the minerals and mineral salts away during the resorption/demineralization process.

Another set of signals cause the over expression of TNF-alpha and RANKL, which directs the pre-osteoclastic cells to differentiate into additional osteoclasts and thereby accelerates the resorption (softening) of bone due to the increase in the number of progenitor cells with activating proteins. Historically, the rate of tooth movement is limited by the number of osteoclasts available to cause bone resorption, at the leading (compression) side of tooth movement.

VEGF speeds up the process of bone metabolism for the resorption/demineralization and then bone formation re-mineralization.

The release of eNOS nitric oxide synthase improves local blood flow.

eNOS and VEGF are responsible for carrying the mineral salts away during the resorption process, which allows the bone to be demineralized (softened) and the tooth to move through the bone. The more the bone resorbs, the more blood vessels are needed to carry the mineral salts away, to allow for a substantial increase in tooth movement.

OPG causes the bone to re-mineralize and the teeth to stabilize in their orthodontic corrected positions. The stimulator and conductive mouthpiece cause an increased release of OPG following the completion of tooth movement, to enhance tooth/bone stability by stimulating increased osteoblastic activity with additional tooth stabilizing bone deposition. This signal is utilized following orthodontic tooth movement to enhance tooth stability through an increase of bone deposition (hardening). The signal will stimulate an increase of osteoblastic activity (greater number of progenitor cells and increased expression of OPG) to strengthen the bone following the completion of tooth movement. This will substantially increase the rate of bone deposition which will lead to improved tooth/bone stability in a significantly shorter period of time.

By using the stimulator to increase the number of osteoclastic cells and specific proteins and by combining these effects in a sequential way, the rate of bone resorption/demineralization is increased. This will result in accelerating tooth movement and therefore a decrease in the length of time for orthodontic treatment.

A bioelectric signal generator (FIG. 1) is used to generate the specific signals typically transmitted via the conductive mouthpiece that cause the specific cells and proteins to be released from cells associated with the gums and bone. The stimulator is programmed with the correct signals in the proper sequence to facilitate bone resorption/demineralization (softening). In severe cases, a micro pump may also be utilized to provide a higher volume of therapeutic agents more rapidly.

The device and method is for the proper signaling and sequencing for recruiting stem cells, having them differentiate into osteoclasts through the release of specific proteins, and to grow additional blood vessels to achieve the acceleration of bone resorption/demineralization for the shortening of orthodontic treatment time. A further micro pump (not shown) is optional and may be used for, e.g., severe craniofacial anomaly cases.

By stimulating the release of the protein OPG (antagonist of RANKL), the osteoclastic bone resorption process is halted and the progenitor cells then become osteoblasts that are responsible for bone remineralization. This facilitates orthodontic stability after the tooth movement portion of treatment is completed.

Figure 1:
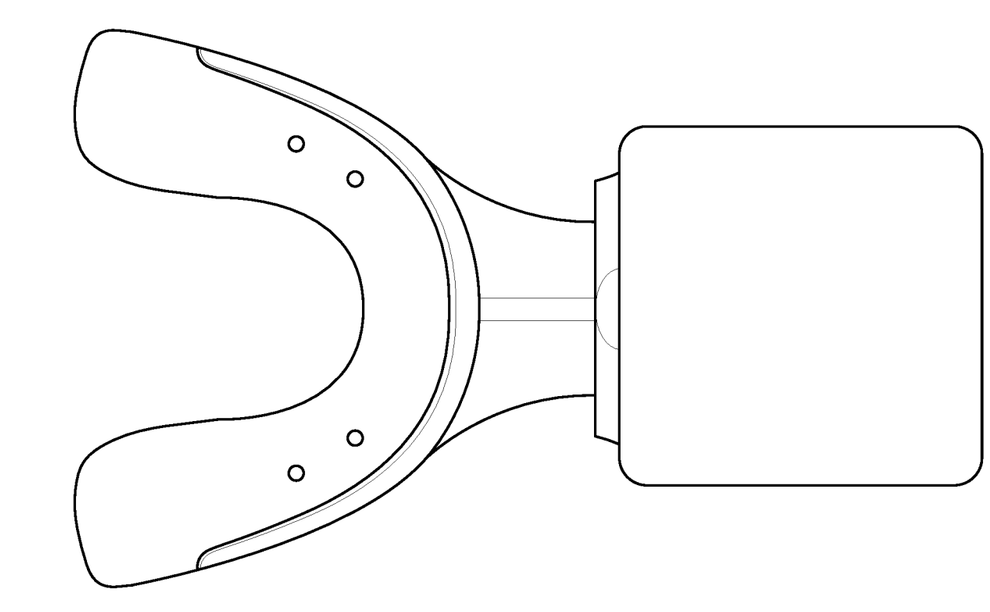
FIG. 1 depicts a programmed bioelectric stimulator for use with the described system.

A bioelectric stimulator is attached to a conductive mouthpiece placed in the mouth for a minimum of 20-40 minutes a day, 3 days a week. The mouthpiece portion can conduct electricity by, e.g., being made of a conductive polymer, having a conductive hydrogel included, by using a conductive tape or wrap (see below), and/or by using conductive metal elements built into the mouth piece in strategic positions (FIG. 1).

Various means of accomplishing electrical conductivity in the mouthpiece are known. For example, electrically conductive adhesive tape is available from 3M of Minnesota. Silicone-based Electrically Conductive Adhesive (ECA) has been developed for the Metal Wrap-Through module technology. Conductive polymers are known in the art, and could be, e.g., linear-backbone "polymer blacks" (polyacetylene, polypyrrole, and polyaniline) and their copolymers. See, also, Kaur et al. "Electrically conductive polymers and composites for biomedical applications," *RSC Adv.*, 2015, 5, 37553-37567 DOI: 10.1039/C5RA01851J, U.S. Pat. No. 8,660,669 (Feb. 25, 2014), CA 2685161 A1 (Oct. 18, 2007), and US 20120156648 (Jun. 21, 2012), the contents of each of which are incorporated herein by this reference.

The bioelectric stimulator is programmed to cause the subject's cells to release SDF-1, M-CSF, RANKL, TNF-alpha, VEGF, etc. in sequence. At periodic intervals, the polarity is reversed and the voltage is dropped to trigger cell differentiation for the remineralization process.

Additionally, the device may be used to help with facial bone graft/reconstruction for people with craniofacial anomalies (cleft lip and palates). Additionally, it may be useful in helping to heal surgeries to the mouth and skull including various titanium type implants. Also, it can be an orthodontic tooth movement accelerator, an orthodontic treatment tooth stabilizer, and/or a craniofacial bone graft healing accelerator.

Generally, the system hereof involves a bioelectric stimulator that controls release of RANKL, TNF-alpha, OPG, SDF-1, HGF, IGF-1, VEGF, eNOS and M-CSF. SDF-1 is generally for recruiting stem cells and maturing blood vessels. If useful, SDF-1, IGF-1, HGF, EGF, PDGF, Activin A+B, Follistatin, Tropoelastin can also be stimulated by the bioelectric stimulator as may GDF-10, GDF-11, Neurogenin 3 and Relaxin.

IGF-1 is for DNA repair. VEGF grows blood vessels eNOS dilates blood vessels.

The micro voltage signal generator may be produced utilizing the same techniques to produce a standard heart pacemaker well known to a person of ordinary skill in the art. An exemplary microvoltage generator is available (for experimental purpose from Cal-X Stars Business Accelerator, Inc. DBA Leonhardt's Launchpads or Leonhardt Vineyards LLC DBA Leonhardt Ventures of Salt Lake City, Utah, US). The primary difference is the special electrical stimulation signals needed to control (which signals are described later herein).

The construction of the electric signal generators, are known in the art and can be obtained from OEM suppliers as well as their accompanying chargers and programmers. The electric signal generators are programmed to produce specific signals to lead to specific protein expressions at precisely the right time for the procedure.

Referring now to FIG. 1, depicted is a bioelectrical stimulator associated with a conductive polymer mouthpiece for use with treatment. Preferably, the bioelectrical stimulator portion of the device is about the size of two quarters (and is available from QIG Greatbatch/Greatbatch, Inc. of Frisco, Tex., US) and is programmable.

What follows are preferred signals.

20-40 minute treatment cycles 2 times a week for 4 weeks and then 3 times a week until tooth movement is completed.

VEGF—Blood vessel sprouting growth ("Kanno Signal")=0.1V applied at a frequency of 50 Hz. Duration 3 minutes.

SDF-1—Stem cell recruiting signal (Leonhardt I Signal)=30 pulses per second with a voltage of 3.5 mV, and successively alternating currents of 700 to 1500 picoamps for one minute, and again with 700 to 1500 picoamps for one minute+stimulated with current of 0.25 mA, pulse duration of 40 pulses/s, pulse width of 100 μs, and frequency of 100 Hz. Duration 7 minutes.

Stem cell proliferation signals (Leonhardt-Chachques)—15 mV and a current of 500 picoamps at 70 pulses per minute for 3 hours+20 pulses per minute, a pulse amplitude of from 2.5-6 volts, and a pulse width of from 0.2-0.7 milliseconds for 3 hours. Duration 3 minutes.

IGF-1 (Genovese+Leonhardt)—3 my with electric frequency of 22 Hz, and electric current of 1 mA for 15 minutes and 3 ma for 15 minutes. Duration 5 minutes.

RANKL/TNF Receptor activator of nuclear factor kappa-B (NF-κB) ligand/TNF Alpha (Genovese+Leonhardt+Marchetto)—3 MV at 2/100 Hz alternating frequency with current of 3 ma > Optional use depending on application to be followed by 15 Hz, 1 Gauss EM field, consisting of 5-millisecond bursts with 5-microsecond pulses followed by 200-μs pulse duration @ 30 Hz and with current amplitude of 140 mA. This would typically be conducted in an orthodontic office setting.

eNOS—Alternating high-frequency (HF) and medium-frequency signals (MF)—Symmetric, biphasic, trapezoid pulses, with 400-μs pulse duration and 1.5/1-s ramp-up/ramp-down duration, respectively. HF consisted of 75 Hz pulses with 6 s on-21 s off for 15 minutes. MF consisted of 45 Hz pulses with 5 s on-12 s off for 15 minutes. Followed by stimulation duration set as 20 min for both 1 Hz and 20 Hz stimulations. For 1 Hz stimulation, stimulation is applied for 9 sec, followed by a 1 sec silent period, a total of 1080 stimulations for 20 min. For 20 Hz stimulation, stimulation is applied for 2 sec, followed by silent period for 28 sec, a total of 1600 stimulations for 20 min. Duration 2 minutes.

The invention is further described with the aid of the following illustrative Example(s).

Example

Orthodontic braces and clear aligners work by applying force to teeth in order to gradually realign them. This force causes a demineralization (softening) of the bone, which allows the tooth to move. Although the time it takes for patients to wear braces or aligners varies considerably, it generally takes on average about 2 years. The described system (see, e.g., FIG. 1) however utilizes bioelectric energy to significantly increase the rate at which teeth move. The system is a removable and non-invasive appliance that a patient wears in his or her mouth for 20-40 minutes every 3 days.

The bioelectric stimulator emits small electric pulses that control expressions of RANKL, SDF-1, HGF, IGF-1, TNF-alpha and VEGF, eNOS and M-CSF and OPG as well as stem cell differentiation. Studies have been completed for all these cells and proteins individually for various applications of regeneration. Previously, studies demonstrated that regular needle injections of RANKL in the area of desired tooth movement, significantly accelerates tooth movement and therefore decreases the time needed to wear braces or aligners.

This bioelectric stimulator achieves much quicker orthodontic treatment results with less pain. Also, the electrical stimulation has a pain reducing affect. When compared to the well-documented tooth movement acceleration approach of using surgical corticotomies, it is faster while removing any morbidity along with eliminating the pain and suffering of surgery. The key to the increased rate is drawing an abundance of the needed cells and proteins to the site of tooth movement to accelerate the demineralization (softening) and re-mineralization (hardening) of bone, thereby allowing teeth to move faster.

One example is SDF-1, a key signal for homing stem cells from the surrounding tissue (bone marrow, gum tissue, fat cells and circulating blood) to come to the treated site to aide in tooth movement. There are many other cells and proteins and cytokines that have an increased expression through specific patented signals, all working to substantially increase the rate of tooth movement.

The described system addresses the desire to reduce (e.g., by half) the time it takes to treat orthodontic patients. The approach is to speed up the normal process of bone demineralization in order to accelerate tooth movement. This described system is completely different than previous devices as it provides clear cut direct control for the release of essential cells and proteins needed for accelerating tooth movement, and with less pain.

The bioelectric stimulator leads to over-expression of SDF-1, which recruits critical progenitor cells and proliferates them in the area of orthodontic tooth movement forces. Concurrently, the progenitor cells are acted upon by the proteins over-expressed via the stimulator. As the increasing number of osteoclastic progenitor cells and the increasing specific proteins combine, the net effect is an increase in the number of osteoclasts. These cells are responsible for the demineralization of the bone and are known to be the limiting factor in tooth movement. The greater number of osteoclasts, the greater the resorption/demineralization and the greater the rate of tooth movement.

As the bone is demineralized, there is a need to remove the mineral salts away from the area. This is achieved by signaling for enhance growth of blood vessels and improved blood flow. This increase in blood vessel growth allows the minerals that are a byproduct of bone resorption to be carried away from the site of bone resorption. As the demineralization reaches a critical amount, tooth movement will take place. The increase rate of bone resorption results in an acceleration of tooth movement and therefore a decrease in the length of time needed for orthodontic treatment.

Once the tooth movement is finalized, the same bioelectric stimulator is programmed to increase the amount of bone remineralization. The pathway is to have an increase of the progenitor cells signaled to the area. Specific proteins can be over expressed simultaneously to act on the progenitor cells to cause the differentiation into osteoblasts, which are responsible for bone deposition. As with the bone resorption pathway, the greater the number of osteoblastic cells the greater the bone deposition. This can result in accelerating the tooth/bone stability and therefore decrease the length of time need for retention. The greater the stability, the less chance for relapse.

The bioelectric stimulator accurately delivers a multitude of signals to the gums and bone. The stimulator is programmed with the correct signals in the proper sequence to facilitate initially bone resorption (softening) followed by bone deposition (remineralization).

The two-pronged approach first works to accelerate tooth movement. The device and method are used for proper signaling with the proper sequence for recruiting stem cells, having them differentiate into osteoclasts, by the release of certain proteins, and to grow additional blood vessels are all necessary for the acceleration of bone resorption and shortening orthodontic treatment time.

The second part of the approach creates greater tooth stability following active tooth movement. The device and method is then used for a different signaling, with the proper sequence for recruiting stem cells, have them differentiate into osteoblasts by the release of certain proteins, and to grow additional blood vessels are all necessary for the acceleration of bone deposition and the shortening of the orthodontic retention time.

The only interchangeable parts are the bioelectric stimulator and the mouthpiece which is a conductive polymer. Different stimulators can be used as well as various types of materials for the mouthpiece to deliver the signals.

Once orthodontic treatment commences, a bioelectric stimulator is attached to a conductive polymer mouthpiece and is placed in the mouth every third day for 20-40 minutes about every other day. The mouthpiece is designed to cover one or both of the dental arches. The stimulator is programmed to cause release of SDF-1, MCSF, RANKL, TNF-alpha and VEGF, eNOS, in sequence during the active portion of treatment. Once the active orthodontic treatment is completed, the same mouth piece is re-programmed to cause release of SDF-1, OPG, VEGF, eNOS to trigger cell differentiation for the remineralization process and enhanced accelerated tooth stability.

REFERENCES (The contents of the entirety of each of which is incorporated herein by this reference.)

Almpani and Kantarci "Nonsurgical Methods for the Acceleration of the Orthodontic Tooth Movement," *Tooth Movement. Front Oral Biol.*, vol. 18, pp 80-91 (Karger, Basel, CH 2016) (DOI:10.1159/000382048), Published online: Nov. 24, 2015.

Dibart et al. "Tissue response during Piezocision-assisted tooth movement: a histological study in rats," *Eur. J. Orthod.* (2014) 36 (4): 457-464; DOI: https://doi.org/10.1093/ejo/cjt079.

Khan et al. "Accelerating Tooth Movement: What Options We Have?" *J. Dent. Health Oral Disord. Ther.* 2016, 5(7): 00181.

M. Yamaguchi, "RANK/RANKL/OPG during orthodontic tooth movement," *Orthod. Craniofac. Res.* 2009 May; 12(2):113-9. doi: 10.1111/j.1601-6343.2009.01444.x.

Nimeri et al. "Acceleration of tooth movement during orthodontic treatment—a frontier in Orthodontics," *Prog. Orthod.* 2013; 14:42; DOI: 10.1186/2196-1042-14-42.

Signature Orthodontics "Accelerated Tooth Movement," http://www.sigortho.com/accelerated-tooth-movement.

Zupan et al. "The relationship between osteoclastogenic and anti-osteoclastogenic pro-inflammatory cytokines differs in human osteoporotic and osteoarthritic bone tissues," *Journal of Biomedical Science*, 2012, 19:28 (DOI: 10.1186/1423-0127-19-28).

Keles et al. "Inhibition of tooth movement by osteoprotegerin vs. pamidronate under conditions of constant orthodontic force," *Eur. J. Oral Sci.* 2007 April; 115(2):131-6.

d'Apuzzo et al. "Biomarkers of Periodontal Tissue Remodeling during Orthodontic Tooth Movement in Mice and Men: Overview and Clinical Relevance," *The Scientific World Journal*, Vol. 2013 (2013), Article ID 105873, 8 pages, http://dx.doi.org/10.1155/2013/105873.

Otero et al. "Expression and Presence of OPG and RANKL mRNA and Protein in Human Periodontal Ligament with Orthodontic Force," *Gene-Regulation-and-Systems-Biology*, 2016, 10, 15-20.

Kanzaki et al. "Local RANKL gene transfer to the periodontal tissue accelerates orthodontic tooth movement," *Gene Therapy* (2006) 13, 678-685.

Vinod Krishnan, Ze'ev Davidovitch (eds.), *Biological Mechanisms of Tooth Movement*, (John Wiley & Sons 2015).

Seifi & Jeszri "Correlation of bone resorption induced by orthodontic tooth movement and expression of RANKL in rats," *Dental Journal*, Vol 26, No 4 (2009).

R. Hamman "Modulation Of RANKL and Osteoprotegerin in Adolescents Using Orthodontic Forces," Masters Thesis, University of Tennessee (2010).

K. Hart, Katherine Ann D.D.S., "RANKL and Osteoprotegerin Levels in Response to Orthodontic Forces" (2012), *Theses and Dissertations* (ETD). Paper 107. http://dx.doi.org/10.21007/etd.cghs.2012.0127.

Giganti et al. "Changes in serum levels of TNF-alpha, IL-6, OPG, RANKL and their correlation with radiographic and clinical assessment in fragility fractures and high energy fractures," *J. Biol. Regul. Homeost. Agents*, 2012 October-December; 26(4):671-80.

Walsh & Choi "Biology of the RANKL-RANK-OPG System in Immunity, Bone, and Beyond," *Front Immunol.* 2014; 5: 511.

Holding et al. "The correlation of RANK, RANKL and TNFα expression with bone loss volume and polyethylene wear debris around hip implants," *Biomaterials* 27(30):5212-9. November 2006.

Chang et al. "Pulsed electromagnetic fields stimulation affects osteoclast formation by modulation of osteoprotegerin, RANK ligand and macrophage colony-stimulating factor," *Journal of Orthopaedic Research*, 23 (2005) 1308-1314.

Jansen et al. "Stimulation of osteogenic differentiation in human osteoprogenitor cells by pulsed electromagnetic fields: an in vitro study" *BMC Musculoskeletal Disorders* (2010) 11:188 DOI: 10.1186/1471-2474-11-188.

Kanzaki et al. "Local OPG gene transfer to periodontal tissue inhibits orthodontic tooth movement." *J. Dent. Res.* 2004; 83:920-925.

Kanzaki et al. "Periodontal ligament cells under mechanical stress induce osteoclastogenesis by receptor activator of nuclear factor kappaB ligand up-regulation via prostaglandin E2 synthesis." *J. Bone Miner. Res.* 2002; 17:210-220.

Kaur et al. "Electrically conductive polymers and composites for biomedical applications," *RSC Adv.*, 2015, 5, 37553-37567 DOI: 10.1039/C5RA01851.1.

What is claimed is:

1. A method of assisting in an orthodontic procedure in a subject of the type involving applying braces or aligners to the subject's teeth, the method comprising:
    obtaining a device comprising:
        a bioelectric stimulator programmed to produce sequential electrical signals, wherein a first electrical signal of said sequential electrical signals is three (3) milliVolt at 2/100 Hz alternating frequency with current of three (3) microAmperes, and,
        electrically associated with the bioelectric stimulator, an electrically conductive mouthpiece comprised of a polymer and constructed to fit over the subject's teeth and in proximity of the subject's gums placing the device over the subject's teeth, and applied braces or aligner(s), and in proximity of the dental gums of the subject via the electrically conductive mouthpiece, and
    applying the first electrical signal to the dental gums of the subject as part of the orthodontic procedure,
    wherein the first electrical signal causes the subject to produce receptor activator of nuclear factor kappa-B ligand ("RANKL") and tumor necrosis factor-alpha ("TNF-α").

2. The method according to claim 1, further comprising utilizing the device to produce a subsequent electrical signal that causes stem cell homing factor ("SDF-1") release in the subject.

3. The method according to claim 2, wherein the subsequent electrical signal is 30 pulses per second with a voltage of 3.5 milliVolt, and successively alternating currents of 700 to 1500 picoamps for one minute, and again with 700 to 1500 picoamps for one minute.

4. The method according to claim 3, further comprising stimulating the subject's dental gums with a current of 0.25 mA, pulse duration of 40 pulses/second, pulse width of 100 µs, and frequency of 100 Hz for a duration of 7 minutes.

5. The method according to claim 1, further comprising utilizing the device to produce a subsequent electrical signal that increases vascular endothelial growth factor ("VEGF") in the subject.

6. The method according to claim 5, wherein the subsequent electrical signal is 0.1V applied at a frequency of 50 Hz for a duration of 3 minutes.

7. The method according to claim 1, further comprising utilizing the device to produce a subsequent electrical signal that causes insulin-like growth factor ("IGF-1") release in the subject.

8. The method according to claim 7, wherein the subsequent electrical signal is 3 milliVolt with electric frequency of 22 Hz, and electric current of 1 microamperes for 15 minutes.

9. The method according to claim 1, further comprising utilizing the device to produce a subsequent electrical signal that causes osteoprotegerin ("OPG") release in the subject.

10. The method according to claim 8, further comprising stimulating the subject's dental gums with a current of 3 microamperes for 15 minutes.

11. The method according to claim 9, wherein the subsequent electrical signal is range 3 milliVolt to 5 milliVolt at a frequency range of 1 to 3 MHz, and a duration range of 30 to 40 mW/cm² for a minimum of 20 to 45 minutes.

12. The method according to claim 1, further comprising:
    applying to the subject's dental gums a 15 Hz, 1 Gauss EM field, consisting of 5-millisecond bursts with 5-microsecond pulses followed by 200-Mµs pulse duration at 30 Hz and with current amplitude of 140 microAmperes for a minimum 20 to 45 minutes.

13. The method according to claim 1, wherein a subsequent electrical signal produced by the device ranges from 3 milliVolt to 5 milliVolt at frequency range 1 to 3 MHz duration range 30 to 40 mW/cm² for a minimum 20 to 45 minutes.

14. The method according to claim 1, wherein the orthodontic procedure comprises applying braces to the subject's teeth.

15. The method according to claim 1, wherein the orthodontic procedure comprises applying an aligner to the subject's teeth.

16. The method according to claim 1, further comprising utilizing the device to produce a subsequent electrical signal that causes eNOS release in the subject.

* * * * *

UNITED STATES PATENT AND TRADEMARK OFFICE
CERTIFICATE OF CORRECTION

PATENT NO. : 10,695,563 B2
APPLICATION NO. : 15/471954
DATED : June 30, 2020
INVENTOR(S) : Leonhardt et al.

Page 1 of 1

It is certified that error appears in the above-identified patent and that said Letters Patent is hereby corrected as shown below:

In the Specification

| | | |
|---|---|---|
| Column 3, | Line 29, | change "3 my to 5 my" to --3 mv to 5 mv-- |
| Column 8, | Line 15, | change "3 my with" to --3 mv with-- |
| Column 11, | Line 52, | change "10.1039/C5RA01851.1." to --10.1039/C5RA01851J.-- |

Signed and Sealed this
Eighth Day of September, 2020

Andrei Iancu
*Director of the United States Patent and Trademark Office*